US00PP10953P

United States Patent [19]

Danziger

[11] Patent Number: Plant 10,953

[45] Date of Patent: Jun. 8, 1999

[54] PETUNIA PLANT NAMED 'DANPETBRI'

[75] Inventor: Gabriel Danziger, Nir Zvi, Israel

[73] Assignee: Danziger — "Dan" Flower Farm, Post Beit Dagan, Israel

[21] Appl. No.: 08/865,891

[22] Filed: May 30, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS 5,523,520 6/1996 Hunsperger ..... 800/200

*Primary Examiner*—Howard J. Locker

*Attorney, Agent, or Firm*—Foley & Lardner

[57] ABSTRACT

The petunia plant named 'Danpetbri' is particularly characterized by its tight, trailing graceful habit, small diameter, clear white flowers with purple veins in the corolla tube, good weather tolerance, and strong growth.

2 Drawing Sheets

The present invention comprises a new and distinct cultivar of petunia, known by the cultivar name 'Danpetbri'.

'Danpetbri' was originated from a hybridization made by the inventor, Gabriel Danziger, in a controlled breeding program in Mishmar Hashiva, Israel in 1995. The male and female parents were unnamed proprietary lines used in the breeding program.

'Danpetbri' was discovered and selected as one flowering plant within the progeny of the stated cross by the inventor Gabriel Danziger in May 1995 in a controlled environment in Mishmar Hashiva.

The first act of asexual reproduction of 'Danpetbri' was accomplished when vegetative cuttings were taken from the initial selection in June 1995 in a controlled environment in Mishmar Hashiva by a technician working under the supervision of the inventor. Horticultural examination of selected units was initiated in September 1995 and has demonstrated that the combination of characteristics as herein disclosed for 'Danpetbri' are firmly fixed and are retained through successive generations of asexual reproduction.

'Danpetbri' has not been observed under all possible environmental conditions. The phenotype may vary somewhat with variations in environment such as temperature, light intensity and day length, without any variations in genotype. The following observations, measurements and comparisons describe the plants grown in Mishmar Hashiva under greenhouse conditions which approximate those generally used in commercial practice.

The following traits have been repeatedly observed and are determined to be basic characteristics of 'Danpetbri' which in combination distinguish this petunia as a new and distinct cultivar:

1. Tight trailing habit.
2. Small diameter flowers with a clear white color.
3. Good weather tolerance including vigorous growth under hot climate conditions. The plant tolerates mild winter conditions and recovers well after heavy rain.
4. Strong growth.
5. When plant is in full flowering, it displays an especially graceful appearance.
6. Plants of 'Danpetbri' can be used in mixed arrangements.

Of the many commercial cultivars known to the inventor, there is none with which the new cultivar can be meaningfully compared.

While the cultivar name of this plant is 'Danpetbri' for purposes of international recognition, it is being marketed in the United States under the tradename "Bright Dream".

In the accompanying photographic drawings,

Sheet 1 is a side perspective view of the new cultivar showing typical flower and foliage characteristics of 'Danpetbri'.

Sheet 2 is a close-up view showing the corolla, throat, and flower vein details. The colors are as true as possible with illustrations of this type.

In the following description color references are made to The Royal Horticultural Society Color Chart. The color values were determined between 10:00–12:00 a.m. in October 1996 under full sunlight at Mishmar Hashiva.

Classification:

*Botanical.*—*Petunia hybrida.*

*Commercial.*—Petunia cultivar 'Danpetbri'.

Plant:

*Growth habit.*—Tight trailing habit.

*Plant height.*—Approximately 10–13 cm.

*Spreading area.*—Approximately 90–103 cm.

*Blooming period.*—Throughout year.

*Branching.*—Trailing growth habit, free, densely branched plant.

*Pinching.*—Pinching is required early in growth to induce a branched plant. Pinching generally delays the first flowering; however, after the initial pinching, flowering is fast and free with no additional pinching required.

Stem:

*Thickness.*—2–3 mm.

*Color.*—Green, R.H.S. 143C.

*Pubescence.*—Yes.

*Branching.*—Free.

*Length of internode.*—15–18 mm.

*Rooting.*—Stems, while attached to the plant, do not root at the nodes when placed in moist soil. Cuttings do root.

Leaf:

*Arrangement on stem.*—Alternate.

*Shape.*—Oval.

*Size.*—Approximately 2.5 cm.

*Thickness.*—1.0 mm.

*Color.*—Upper surface R.H.S. 146B.

*Pubescence.*—Yes.

*Markings.*—None.

Flower:

*Orientation at opening.*—Upright.

*Type.*—Single.

*Shape.*—Regular rounded corolla united with 5 lobes and a long straight tube about 42 mm in length.

*Diameter.*—35 mm; relatively small.

*Color.*—Upper surface: Upper surface R.H.S. 155C with veins and throat R.H.S. 86A. Lower surface: White (R.H.S. 155D) infused with purple coloration.

*Calyx.*—Five pubescent sepals, about 12 mm in length, coloration is green (closest to R.H.S. 146B).

*Peduncle.*—Length: 18 mm. Color: Green.

*Reproductive organs.*—Pistil: Number: 1. Color: Green. Stamens: Number: 5. Anther: Gray. Filament: Green.

Other characteristics: The cultivar does not set seeds.

Disease resistance: 'Danpetbri' has not been shown to be unusually susceptible to common diseases of petunia, and is resistant to most leaf diseases.

I claim:

1. A new and distinct cultivar of petunia plant named 'Danpetbri' as herein shown and described.

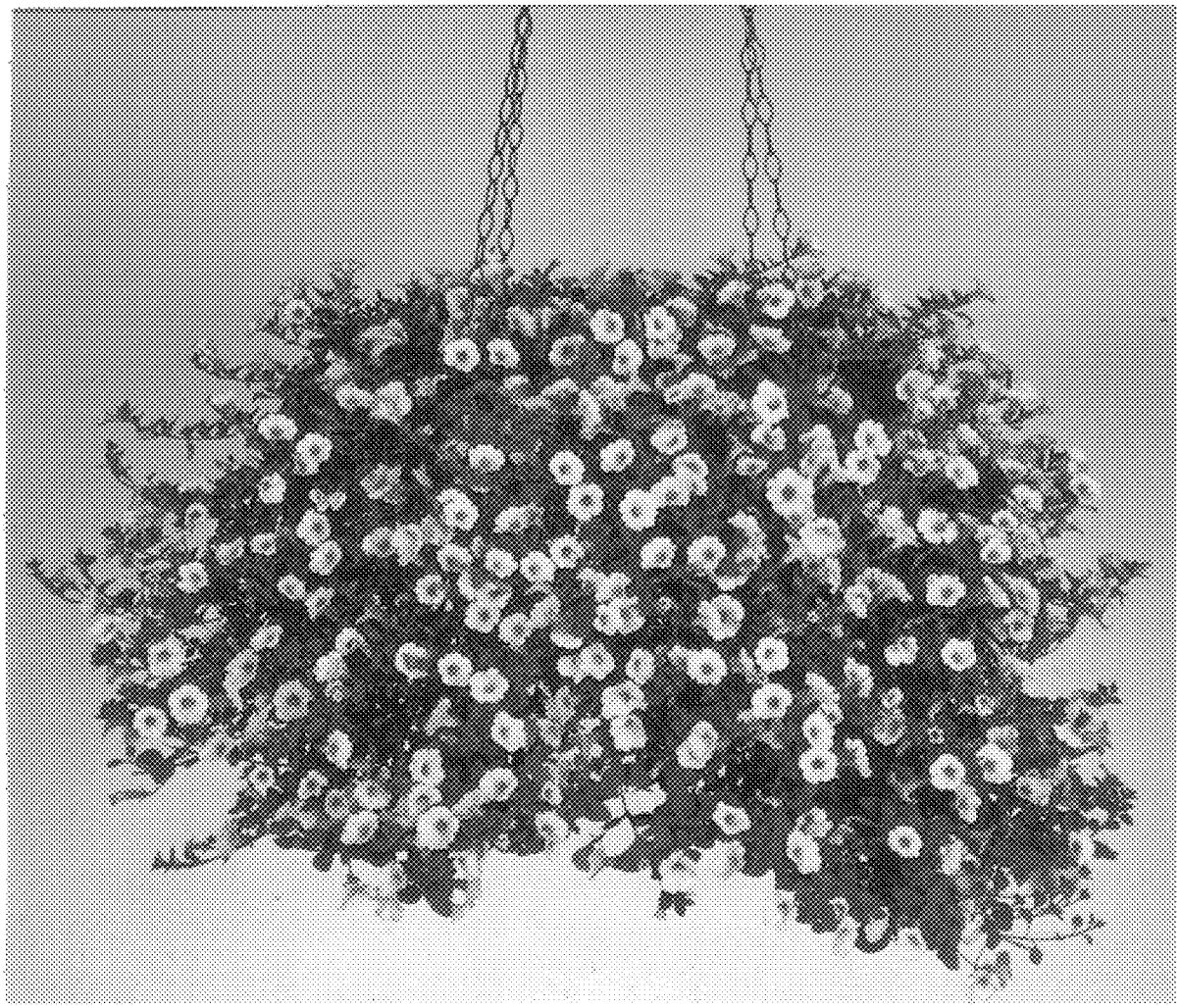

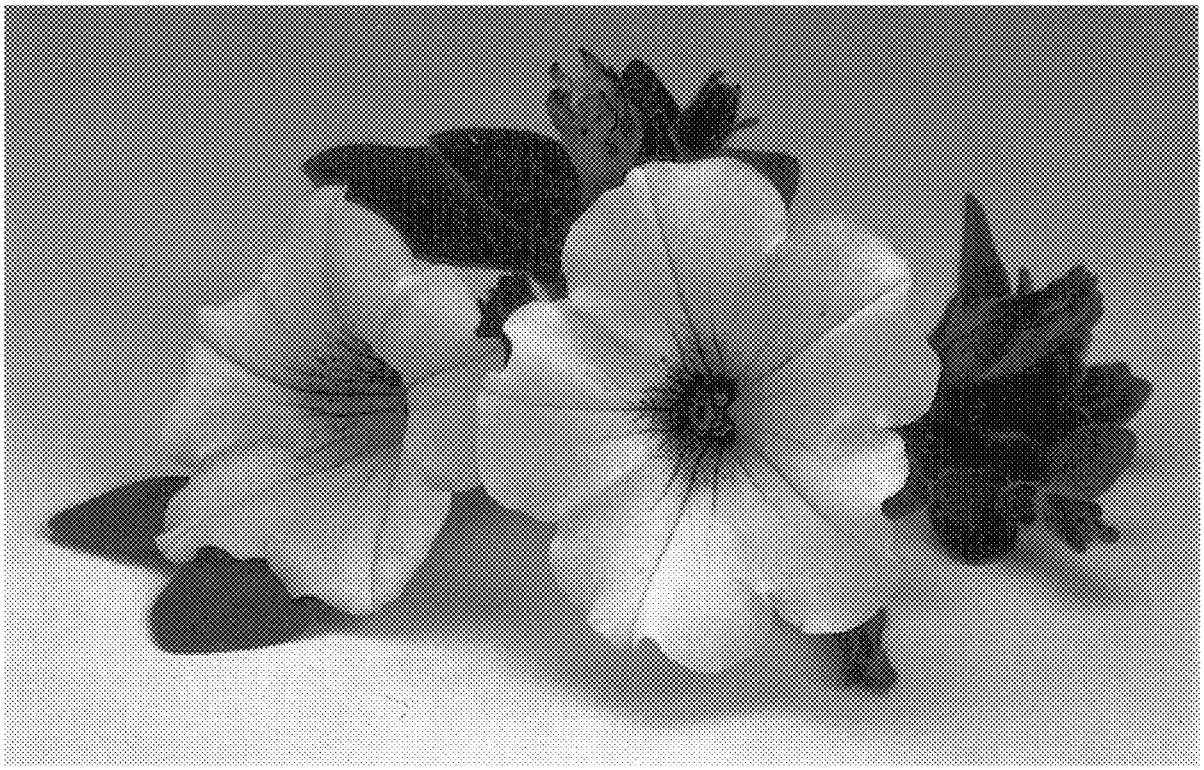

* * * * *